(12) United States Patent
Hasegawa (10) Patent No.: US 11,395,710 B2
(45) Date of Patent: Jul. 26, 2022

(54) TREATMENT TOOL

(71) Applicant: OLYMPUS CORPORATION, Hachioji (JP)

(72) Inventor: Mitsuaki Hasegawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 310 days.

(21) Appl. No.: 16/748,996

(22) Filed: Jan. 22, 2020

(65) Prior Publication Data

US 2020/0170738 A1    Jun. 4, 2020

Related U.S. Application Data

(63) Continuation of application No. PCT/JP2017/028908, filed on Aug. 9, 2017.

(51) Int. Cl.
*A61B 34/00* (2016.01)
*A61B 1/005* (2006.01)
(Continued)

(52) U.S. Cl.
CPC ............ *A61B 34/74* (2016.02); *A61B 1/0052* (2013.01); *A61B 34/71* (2016.02);
(Continued)

(58) Field of Classification Search
CPC ....... A61B 34/74; A61B 1/0052; A61B 34/71; A61B 2017/00296; A61B 2017/00318;
(Continued)

(56) References Cited

U.S. PATENT DOCUMENTS 5,327,905 A * 7/1994 Avitall ............... A61B 18/1492
600/381
5,354,297 A    10/1994 Avitall
(Continued)

FOREIGN PATENT DOCUMENTS

CA    2674520 A1    2/2010
EP    1561413 A1    8/2005
(Continued)

OTHER PUBLICATIONS

Oct. 17, 2017 International Search Report issued in International Application No. PCT/JP2017/028902.
(Continued)

*Primary Examiner* — Brian T Gedeon
*Assistant Examiner* — Joshua Andrew Schum-Houck
(74) *Attorney, Agent, or Firm* — Oliff PLC (57) ABSTRACT

A treatment tool includes an elongated shaft that has a bending mechanism at a distal end thereof; a bending operation part that is connected to a proximal-end side of the shaft in order to operate the bending mechanism; a connection sleeve that is provided at a connection section of the bending operation part where the bending operation part and the shaft are connected, and that rotatably holds the shaft; a rotation operation member that is provided at the proximal-end side of the shaft and that rotates the shaft; and a stopper member that can be made to slide outside the connection sleeve along a direction of a longitudinal axis of the shaft and that is engaged with both the rotation operation member and the connection sleeve at a specific position in a range of movement thereof, thereby locking rotation of the shaft with respect to the connection sleeve.

16 Claims, 11 Drawing Sheets

(51) Int. Cl.
*A61M 25/01* (2006.01)
*A61B 17/00* (2006.01)

(52) U.S. Cl.
CPC ............... *A61B 2017/0034* (2013.01); *A61B 2017/00296* (2013.01); *A61B 2017/00318* (2013.01); *A61B 2017/00367* (2013.01); *A61M 25/01* (2013.01); *A61M 25/0136* (2013.01)

(58) Field of Classification Search
CPC .. A61B 2017/0034; A61B 2017/00367; A61B 17/29; A61M 25/01; A61M 25/0136
See application file for complete search history.

(56) References Cited

U.S. PATENT DOCUMENTS

| | | | |
|---|---|---|---|
| 5,642,736 | A | 7/1997 | Avitall |
| 6,113,556 | A | 9/2000 | Avitall |
| 2003/0125663 | A1* | 7/2003 | Coleman ........... A61M 25/0136 604/95.04 |
| 2004/0019352 | A1 | 1/2004 | Kidooka |
| 2005/0187575 | A1 | 8/2005 | Hallbeck et al. |
| 2005/0250989 | A1 | 11/2005 | Suzuki |
| 2007/0232858 | A1* | 10/2007 | Macnamara ......... A61B 1/0052 600/149 |
| 2007/0287993 | A1* | 12/2007 | Hinman ................. A61B 17/29 606/1 |
| 2008/0046000 | A1 | 2/2008 | Lee et al. |
| 2008/0065116 | A1* | 3/2008 | Lee .................... A61B 17/2909 606/142 |
| 2009/0312605 | A1 | 12/2009 | Hallbeck et al. |
| 2010/0030018 | A1* | 2/2010 | Fortier ............... A61B 18/1445 600/104 |
| 2010/0168722 | A1 | 7/2010 | Lee et al. |
| 2010/0228235 | A1 | 9/2010 | Lee et al. |
| 2011/0184459 | A1 | 7/2011 | Malkowski et al. |
| 2011/0196419 | A1 | 8/2011 | Cooper |
| 2012/0245567 | A1 | 9/2012 | Lee et al. |
| 2013/0190566 | A1 | 7/2013 | Miyoshi et al. |
| 2013/0317522 | A1 | 11/2013 | Nishizawa et al. |
| 2014/0066978 | A1 | 3/2014 | Hallbeck et al. |
| 2015/0164524 | A1 | 6/2015 | Malkowski et al. |
| 2016/0256183 | A1 | 9/2016 | Cooper |
| 2016/0353979 | A1 | 12/2016 | Hashizume et al. |

FOREIGN PATENT DOCUMENTS

| | | |
|---|---|---|
| EP | 2151204 A1 | 2/2010 |
| EP | 2702923 A1 | 3/2014 |
| EP | 2754400 A1 | 7/2014 |
| EP | 3181069 A1 | 6/2017 |
| JP | H07-504834 A | 6/1995 |
| JP | 2005-218497 A | 8/2005 |
| JP | 2007-526805 A | 9/2007 |
| JP | 2010-500149 A | 1/2010 |
| JP | 4402313 B2 | 1/2010 |
| JP | 2010-36039 A | 2/2010 |
| JP | 2010-503457 A | 2/2010 |
| JP | 4420593 B2 | 2/2010 |
| JP | 2013-518665 A | 5/2013 |
| JP | 2013-176651 A | 9/2013 |
| JP | 5701339 B2 | 4/2015 |
| JP | 2015-128536 A | 7/2015 |
| WO | 1993/15790 A1 | 8/1993 |
| WO | 2005/079333 A2 | 9/2005 |
| WO | 2007/146894 A2 | 12/2007 |
| WO | 2008/020964 A2 | 2/2008 |
| WO | 2008/033240 A2 | 3/2008 |
| WO | 2011/097095 A1 | 8/2011 |
| WO | 2012/173082 A1 | 12/2012 |
| WO | 2013/35870 A1 | 3/2013 |
| WO | 2015/087998 A1 | 6/2015 |
| WO | 2019/030846 A1 | 2/2019 |

OTHER PUBLICATIONS

Oct. 17, 2017 International Search Report issued in International Application No. PCT/JP2017/028908.

Oct. 17, 2017 Written Opinion of the International Searching Authority issued in International Application No. PCT/JP2017/028908.

Oct. 17, 2017 Written Opinion of the International Searching Authority issued in International Application No. PCT/JP2017/028902.

U.S. Appl. No. 16/773,244, filed Jan. 27, 2020 in the name of Hasegawa.

* cited by examiner

TREATMENT TOOL

CROSS-REFERENCE TO RELATED APPLICATIONS

This is a continuation of International Application PCT/JP2017/028908 which is hereby incorporated by reference herein in its entirety.

TECHNICAL FIELD

The disclosed embodiments relate to a treatment tool.

BACKGROUND

A treatment tool may include: an elongated shaft that has a bending mechanism at a distal-end section; a handle that is connected to the proximal end of the shaft; and a bending operation part and a rotation operation part that are provided between the shaft and the handle). The bending operation part is used to perform a bending operation on the bending mechanism of the shaft, and the rotation operation part is used to rotate the shaft with respect to the handle.

The rotation operation part may be provided between the bending operation part and the handle and be configured so as to rotate the bending operation part and the shaft together. However, when the shaft is twisted about its longitudinal axis in the body, this may cause a deviation between operation of the handle and a bending direction of the bending mechanism in an endoscopic image.

SUMMARY

In one aspect of the disclosed embodiments, a treatment tool includes: an elongated shaft that has a bending mechanism at a distal end thereof; a bending operation part that is connected to a proximal-end side of the shaft in order to operate the bending mechanism; a connection sleeve that is provided at a connection section of the bending operation part where the bending operation part and the shaft are connected, and that rotatably holds the shaft; a rotation operation member that is provided at the proximal-end side of the shaft and that rotates the shaft; and a stopper member that can be made to slide outside the connection sleeve along a direction of a longitudinal axis of the shaft and that is engaged with both the rotation operation member and the connection sleeve at a specific position in a range of movement thereof, thereby locking rotation of the shaft with respect to the connection sleeve.

The disclosed embodiments also include an operation method for a treatment tool that includes: an elongated shaft that has a bending mechanism at a distal end thereof; and a bending operation part that rotatably holds the shaft at a proximal-end side of the shaft in order to perform a bending operation on the bending mechanism. The method includes locking rotation of the shaft with respect to the bending operation part; inserting the shaft into a body of a patient; after inserting the shaft into the body of the patient, releasing the lock when a deviation occurs in the correspondence relationship between operation of the bending operation part and a bending direction of the bending mechanism due to twisting of the shaft; in a state in which the lock has been released, rotating the shaft, through operation of a rotation operation member that is provided on the shaft, with respect to the bending operation part, thereby adjusting the correspondence relationship between the operation of the bending operation part and the bending direction of the bending mechanism; and locking again the rotation of the shaft, the rotation being performed by the rotation operation member.

DETAILED DESCRIPTION OF EMBODIMENTS

Treatment tools 1 according to an embodiment of the disclosed embodiments will be described below with reference to the drawings.

Figure 1:
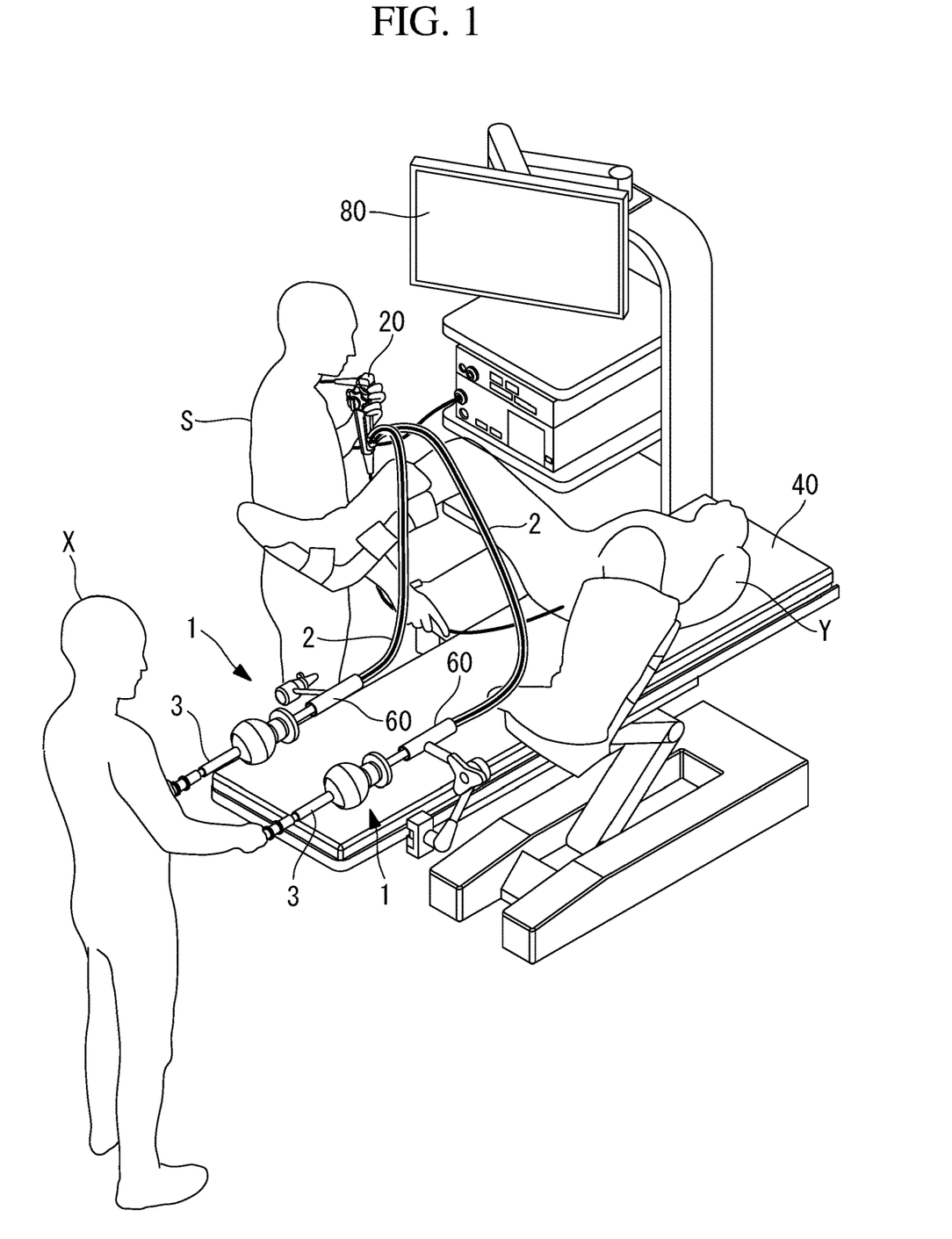
FIG. 1 is a view showing the overall configuration of a surgical system that includes treatment tools according to a disclosed embodiment.
Figure 2:
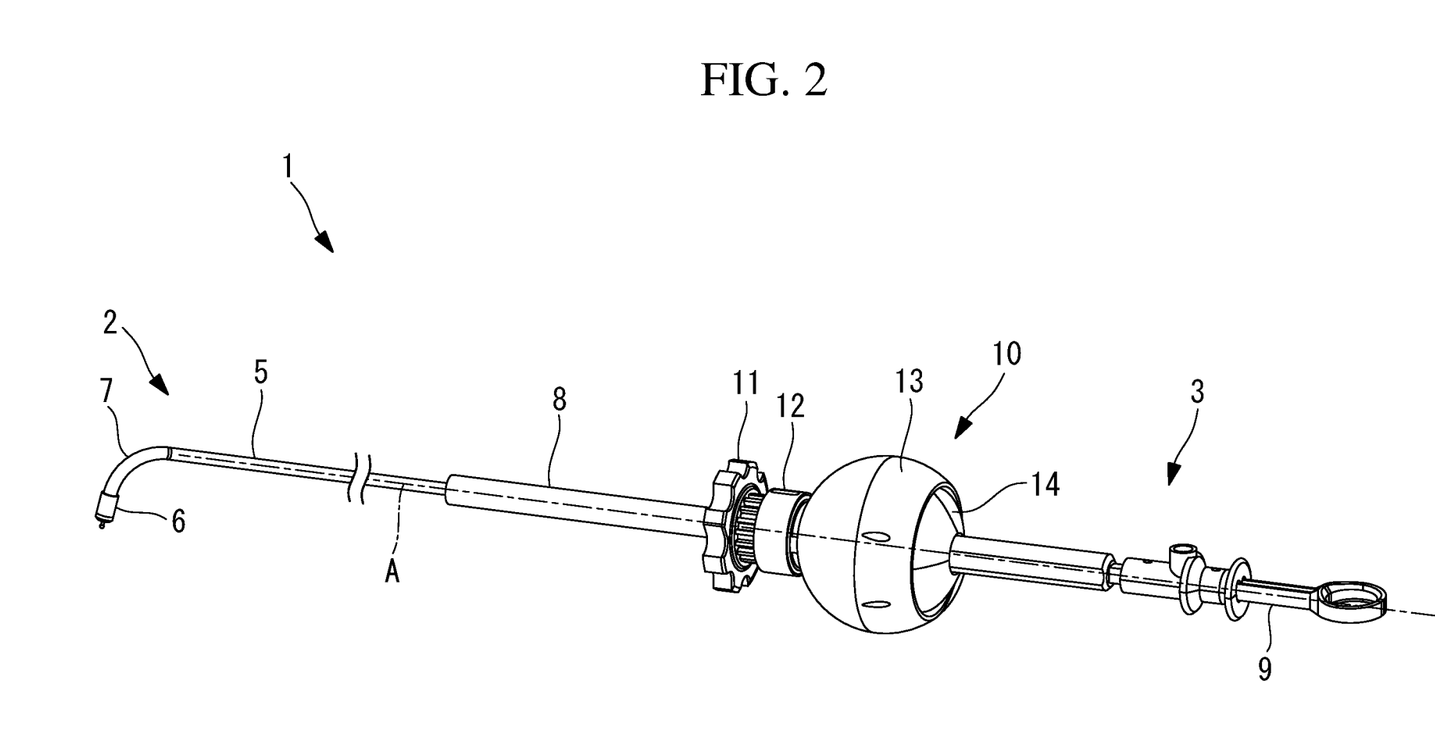
FIG. 2 is a view showing the overall configuration of each of the treatment tools shown in FIG. 1.

As shown in FIGS. 1 and 2, each of the treatment tools 1 of this embodiment includes: an elongated shaft 2 that has a bending section (bending mechanism) 7 at a distal end and that is inserted into the body; an operation unit 3 that is connected to a proximal end of the shaft 2 and that is manually operated by an operator X; and wires 4 (see FIG. 4) that connect the bending section 7 and the operation unit 3 by passing through the inside of the shaft 2 and with which the bending section 7 is bent in accordance with an operation performed on the operation unit 3.

FIG. 1 is a view showing the overall configuration of a surgical system that includes the treatment tools 1 of this embodiment. As shown in FIG. 1, the surgical system includes: an endoscope 20 that is operated by a scopist S; the treatment tools 1, which are operated by the operator X; treatment-tool holders 60 that are fixed to a bed 40 on which a patient Y lies and that support the treatment tools 1; and a display unit 80 that displays an endoscopic image to be observed by means of the endoscope 20. The treatment-tool holders 60 are cylindrical members through which the shafts 2 are made to pass. The shafts 2 are inserted into the body of the patient Y via treatment-tool channels provided on the endoscope 20 or external channels attached to the endoscope 20. FIG. 1 shows an example case in which the endoscope 20 has the two treatment-tool channels, and the operator X operates the two treatment tools 1 with both hands. While observing end effectors provided at the distal ends of the shafts 2 by means of the endoscope 20, the operator X can adjust the positions and the orientations of the end effectors through operation of the operation units 3, which are disposed outside the body.

As shown in FIG. 2, each of the shafts 2 includes: an elongated flexible section 5 that has flexibility; a distal-end section 6 that is disposed at a position close to a distal end of the flexible section 5; and the bending section 7, which connects the flexible section 5 and the distal-end section 6 and which can be bent in a direction intersecting a longitudinal axis A of the flexible section 5.

An end effector (for example, forceps or knife) used to treat living tissue is provided at the distal-end section 6.

In the flexible section 5, four wires 4 that respectively correspond to upper, lower, left, and right sides of the bending section 7 are disposed around the longitudinal axis A of the flexible section 5 at approximately equal intervals in the circumferential direction. The vertical direction and the horizontal direction of the bending section 7 are each perpendicular to the longitudinal axis A of the flexible section 5 and are perpendicular to each other. A distal-end section of each of the wires 4 is fixed to the bending section 7 at a position away from the longitudinal axis A in a direction intersecting the longitudinal axis A, and a proximal-end section of each of the wires 4 is fixed to a ball (to be described later) of the operation unit 3. Each of the wires 4 can be advanced and retracted along the longitudinal axis A of the flexible section 5, and the bending section 7 is bent such that the wire 4 that is retracted toward the proximal end is located radially inward.

The flexible section 5 includes a tubular inner sheath 5a (See FIG. 4) and a tubular outer sheath 5b (See FIG. 4) that covers an outer side of the inner sheath 5a. The inner sheath 5a and the outer sheath 5b each have such flexibility as to allow twist deformation about the longitudinal axis A.

Figure 4:
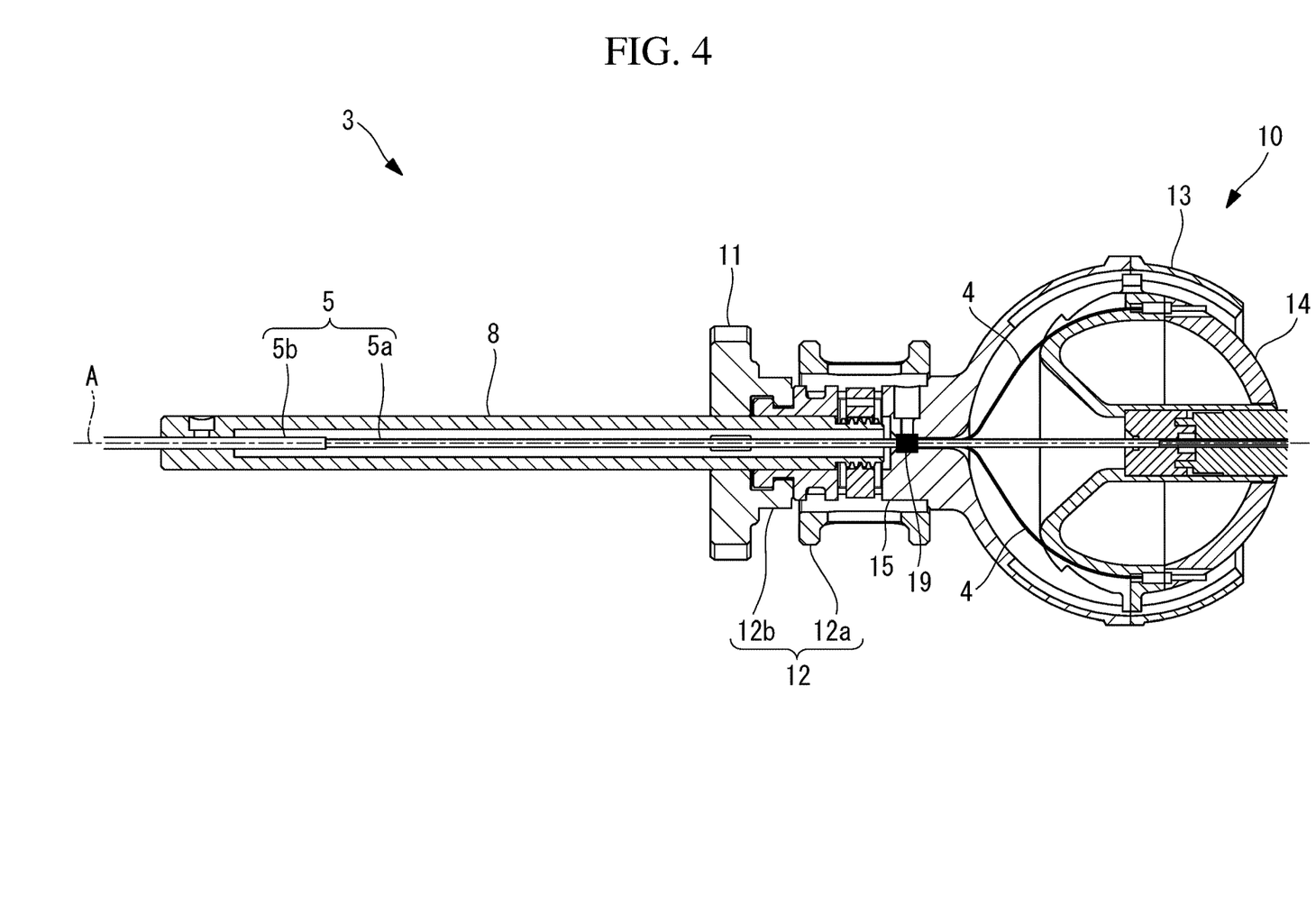
FIG. 4 is a longitudinal sectional view of the operation unit shown in FIG. 3 cut along the longitudinal axis.

A distal-end section of the outer sheath 5b is fixed to a proximal-end section of the bending section 7, and a proximal-end section of the outer sheath 5b is fixed to a distal-end section of a rotating shaft 8 (to be described later) of the operation unit 3.

The inner sheath 5a is a multi-lumen tube having at least four lumens penetrating in the longitudinal direction, and the wires 4 are inserted into the lumens on a one-to-one basis. A distal-end section of the inner sheath 5a is fixed to the distal-end section of the outer sheath 5b, and a proximal-end section of the inner sheath 5a is drawn from the proximal end of the outer sheath 5b and is disposed further toward the proximal end than the rotating shaft 8. Sections of the inner sheath 5a other than the distal-end section are not fixed to the outer sheath 5b, thus allowing twist deformation of the inner sheath 5a about the longitudinal axis A in the outer sheath 5b independently of the outer sheath 5b.

Figure 3:
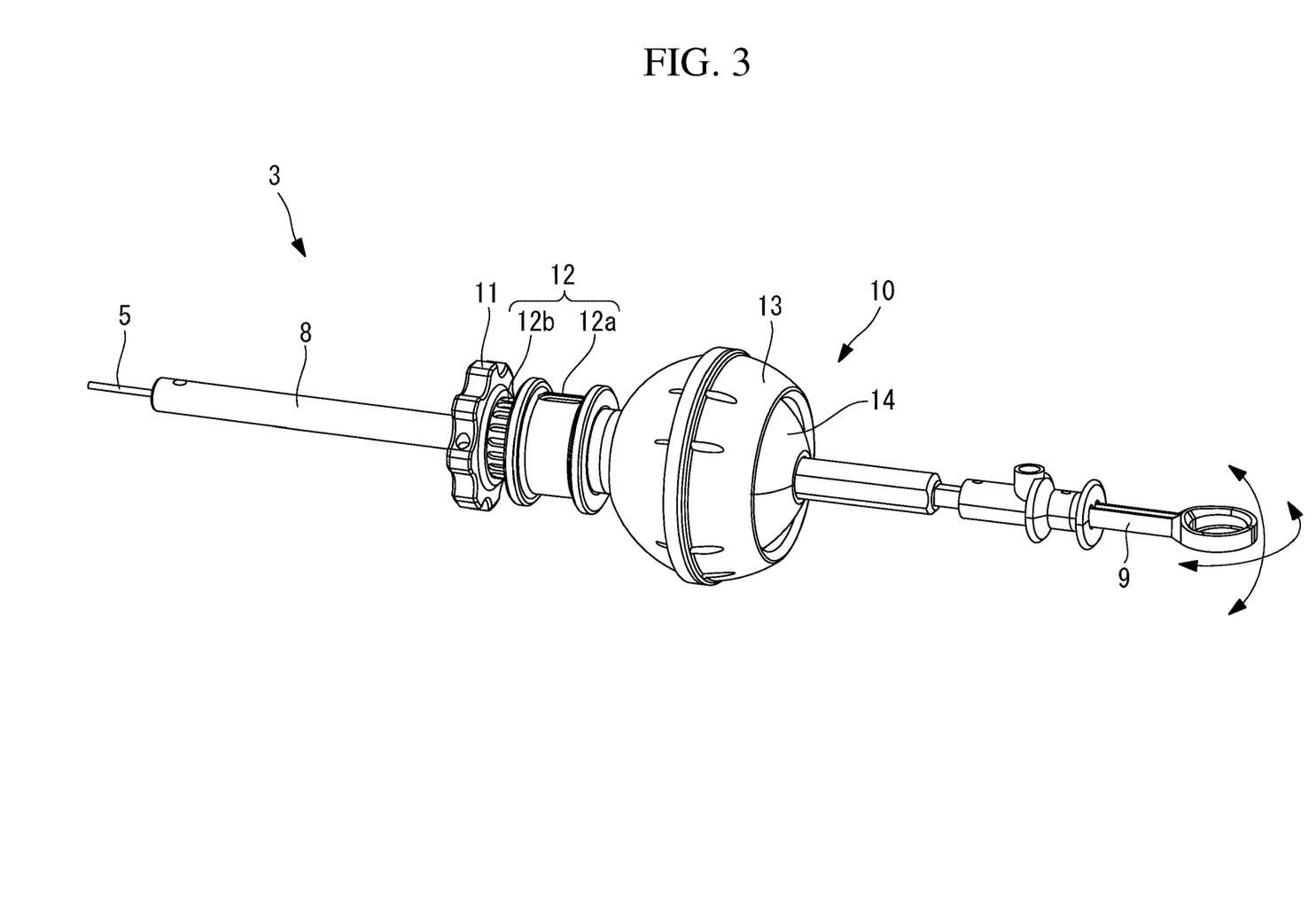
FIG. 3 is an enlarged view of an operation unit of the treatment tool shown in FIG. 2.

As shown in FIGS. 3 and 4, the operation unit 3 includes: the rotating shaft 8, which is hard and which extends coaxially with the flexible section 5; an operation handle 9 that is disposed at the proximal-end side of the rotating shaft 8 and that is gripped by the operator X; a bending operation part (operation part) 10 that is provided between the rotating shaft 8 and the operation handle 9 and that is used to bend the bending section 7; a rotation operation part 11 that is provided integrally with the rotating shaft 8 and that is used to rotate the shafts 2 and 8; and a rotation lock part (lock mechanism) 12 that is used to lock the rotation of the rotation operation part 11.

As shown in FIG. 4, the rotating shaft 8 has a through-hole penetrating along the longitudinal axis A. The proximal-end section of the outer sheath 5b is inserted into the rotating shaft 8. The inner sheath 5a, which is drawn from the proximal end of the outer sheath 5b in the rotating shaft 8, is fixed with respect to a socket 13 (to be described later) of the bending operation part 10, at a fixing part 19 that is located further toward the proximal end than the rotating shaft 8.

The bending operation part 10 has a ball joint structure that includes the nearly spherical hollow socket 13 and the nearly spherical ball (operation member) 14 that is rotatably engaged inside the socket 13.

The socket 13 has a shape obtained by cutting out a proximal-end side of a sphere, in a plane perpendicular to the longitudinal axis of the rotating shaft 8, and is open at a proximal-end surface thereof. The ball 14 is supported on an inner surface of the socket 13 such that the center of the ball 14 matches the center of the socket 13, and the ball 14 can be rotated in an arbitrary direction about the center, with respect to the socket 13.

The operation handle 9 has a substantially straight rod shape, is connected to an outer surface of the ball 14, the outer surface being exposed from the proximal-end surface of the socket 13, and extends toward the opposite side from the shaft 8 and the socket 13. The operation handle 9 is tilted in an arbitrary direction about the center of the socket 13 and the ball 14 through rotation of the ball 14 in the socket 13.

The four wires 4, which are drawn from the proximal end of the inner sheath 5a, are routed between the inner surface of the socket 13 and an outer surface of the ball 14. The proximal-end sections of the four wires 4 are fixed to the outer surface of the ball 14 at positions that are arranged at equal intervals in the circumferential direction around the longitudinal axis A.

The operator X tilts the operation handle 9 in a direction intersecting the longitudinal axis A to rotate the ball 14 inside the socket 13, thereby making it possible to pull the wire 4 that corresponds to the tilt direction of the operation handle 9, thus bending the bending section 7. For example, when the operation handle 9 is tilted in the right direction, rotation (pivoting) of the ball 14 in the right direction pulls the left wire 4 and pushes the right wire 4, thus bending the bending section 7 toward the left.

A cylindrical connection sleeve (rotation mechanism) 15 that extends toward the distal end (the shafts 2 and 8) along the longitudinal axis A and into which the proximal-end section of the rotating shaft 8 is inserted so as to be rotatable about the longitudinal axis A is connected to the socket 13. The rotating shaft 8 and the bending operation part 10 are held by the connection sleeve 15 so as to be rotatable relative to each other about the longitudinal axis A.

The rotation operation part 11 is a rotating handle that is fixed to the proximal-end section of the rotating shaft 8 and that is provided coaxially with the shafts 2 and 8. The bending section 7 is rotated about the longitudinal axis through rotation of the rotation operation part 11 about the longitudinal axis A. Specifically, through rotation of the rotation operation part 11, the rotating shaft 8 is rotated about the longitudinal axis A with respect to the bending operation part 10 and the operation handle 9, and the proximal-end section of the outer sheath 5b, which is connected to the rotating shaft 8, is rotated about the longitudinal axis A. The outer sheath 5b is twisted about the longitudinal axis A, thereby transmitting the rotation of the proximal-end section of the outer sheath 5b to the distal-end section of the outer sheath 5b. Then, the bending section 7, which is fixed to the distal-end section of the outer sheath 5b, is rotated about the longitudinal axis A.

At this time, although the distal-end section of the inner sheath 5a, which is fixed to the distal-end section of the outer sheath 5b, is rotated in accordance with the rotation of the rotation operation part 11, the proximal-end section of the inner sheath 5a, which is fixed with respect to the socket 13 at the fixing part 19, which is located further toward the proximal end than the rotating shaft 8, is not rotated. Therefore, the inner sheath 5a and the wires 4 are twisted about the longitudinal axis A at a side further toward the distal end than the fixing part 19, and the wires 4 are not twisted about the longitudinal axis A at a side further toward the proximal end than the fixing part 19. Accordingly, in the bending operation part 10, which is located further toward the proximal end than the fixing part 19, the positions of the four wires 4 about the longitudinal axis A are maintained irrespective of the rotations of the shafts 2 and 8.

Figure 5A:
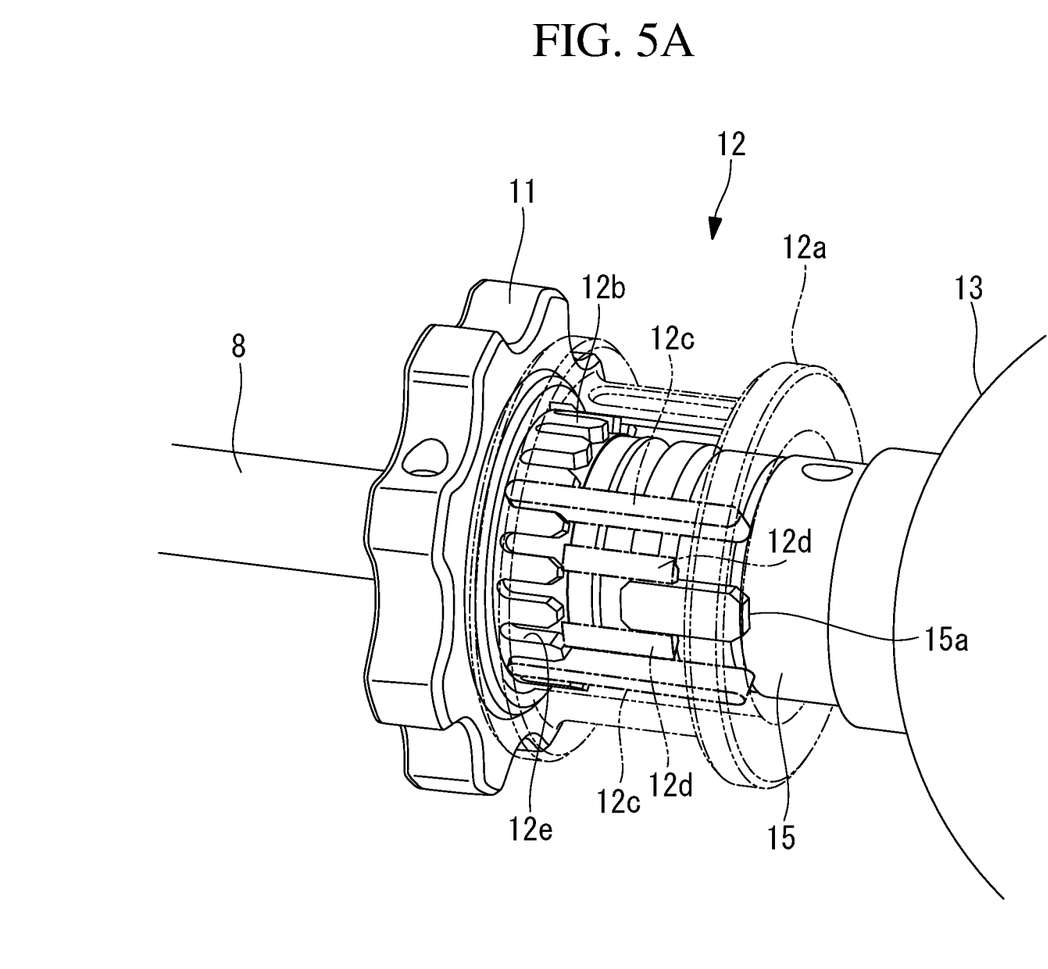
FIG. 5A is a view showing the configuration of a rotation lock part and shows a state in which a stopper is located at a lock position.
Figure 5B:
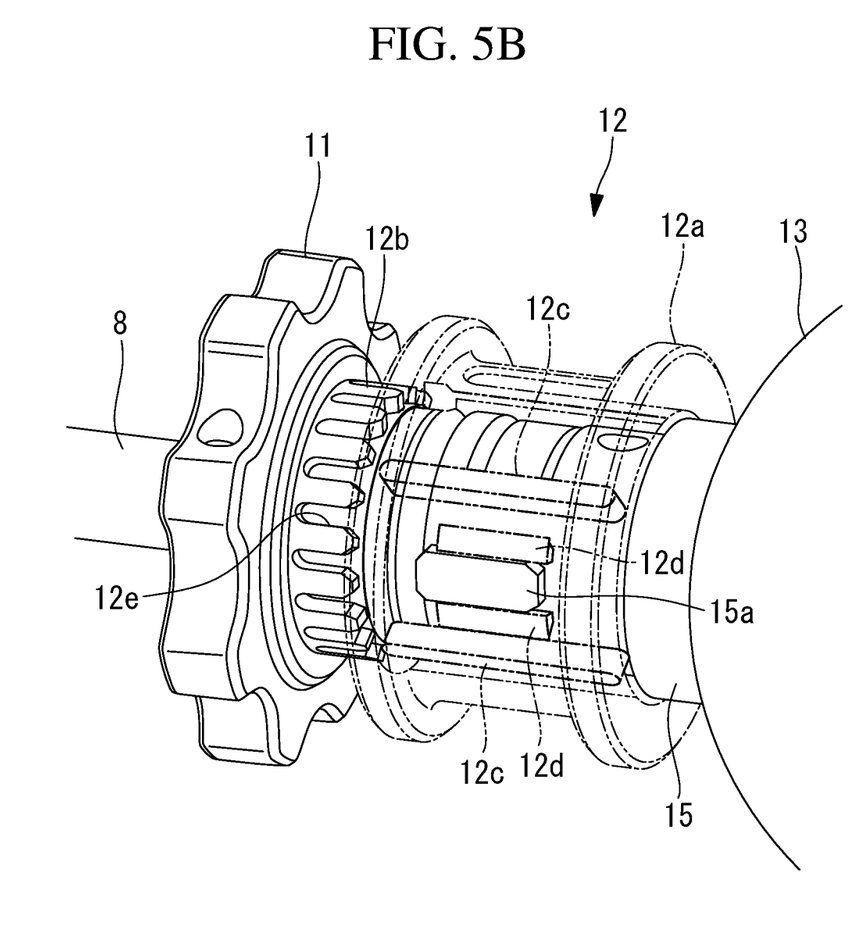
FIG. 5B is a view showing the configuration of the rotation lock part and shows a state in which the stopper is located at a release position.

As shown in FIGS. 5A and 5B, the rotation lock part 12 includes: a cylindrical stopper 12a that is disposed outside the connection sleeve 15 and that locks and releases rotation of the rotation operation part 11 by being made to slide along the longitudinal axis A between a lock position (see FIG. 5A) and a release position (see FIG. 5B); and an engagement ring 12b that is provided on the rotation operation part 11 and that is engaged with locking protrusions 12c that are provided on an inner circumferential surface of the stopper 12a, in the circumferential direction around the longitudinal axis A.

A pair of engagement protrusions 12d that are arranged with a space therebetween in the circumferential direction are provided on the inner circumferential surface of the stopper 12a, and a guide protrusion 15a that extends in the direction along the longitudinal axis A and that is fitted between the pair of engagement protrusions 12d is provided on an outer circumferential surface of the connection sleeve 15. Although the pair of engagement protrusions 12d can be moved along the guide protrusion 15a in the direction along the longitudinal axis A, rotation thereof about the longitudinal axis A is locked by the guide protrusion 15a. Accordingly, the stopper 12a is mounted on the outer circumferential surface of the connection sleeve 15 so as not to be rotated about the longitudinal axis A with respect to the connection sleeve 15 while being allowed to slide along the outer circumferential surface of the connection sleeve 15 in the direction along the longitudinal axis A.

The locking protrusions 12c protrude radially inward from the inner circumferential surface of the stopper 12a and extend in the direction along the longitudinal axis A.

The engagement ring 12b is a toroidal member that is fixed to the proximal end of the rotation operation part 11 and that is provided coaxially with the rotating shaft 8 and the rotation operation part 11, and grooves 12e that extend from a proximal-end surface of the engagement ring 12b in the direction along the longitudinal axis A and into which the protrusions 12c are fitted in the direction along the longitudinal axis A are formed in the engagement ring 12b. The many grooves 12e are provided at intervals in the circumferential direction of the engagement ring 12b.

As shown in FIG. 5A, at the lock position, the protrusions 12c of the stopper 12a are fitted into any of the grooves 12e, thereby locking the rotation of the rotation operation part 11 with respect to the bending operation part 10 and the operation handle 9. On the other hand, as shown in FIG. 5B, at the release position, which is closer to the proximal end than the lock position is, the protrusions 12c are disposed further toward the proximal end than the grooves 12e, thereby allowing the rotation of the rotation operation part 11 with respect to the bending operation part 10 and the operation handle 9.

Next, a surgical method using the treatment tool 1 will be described.

Figure 6:
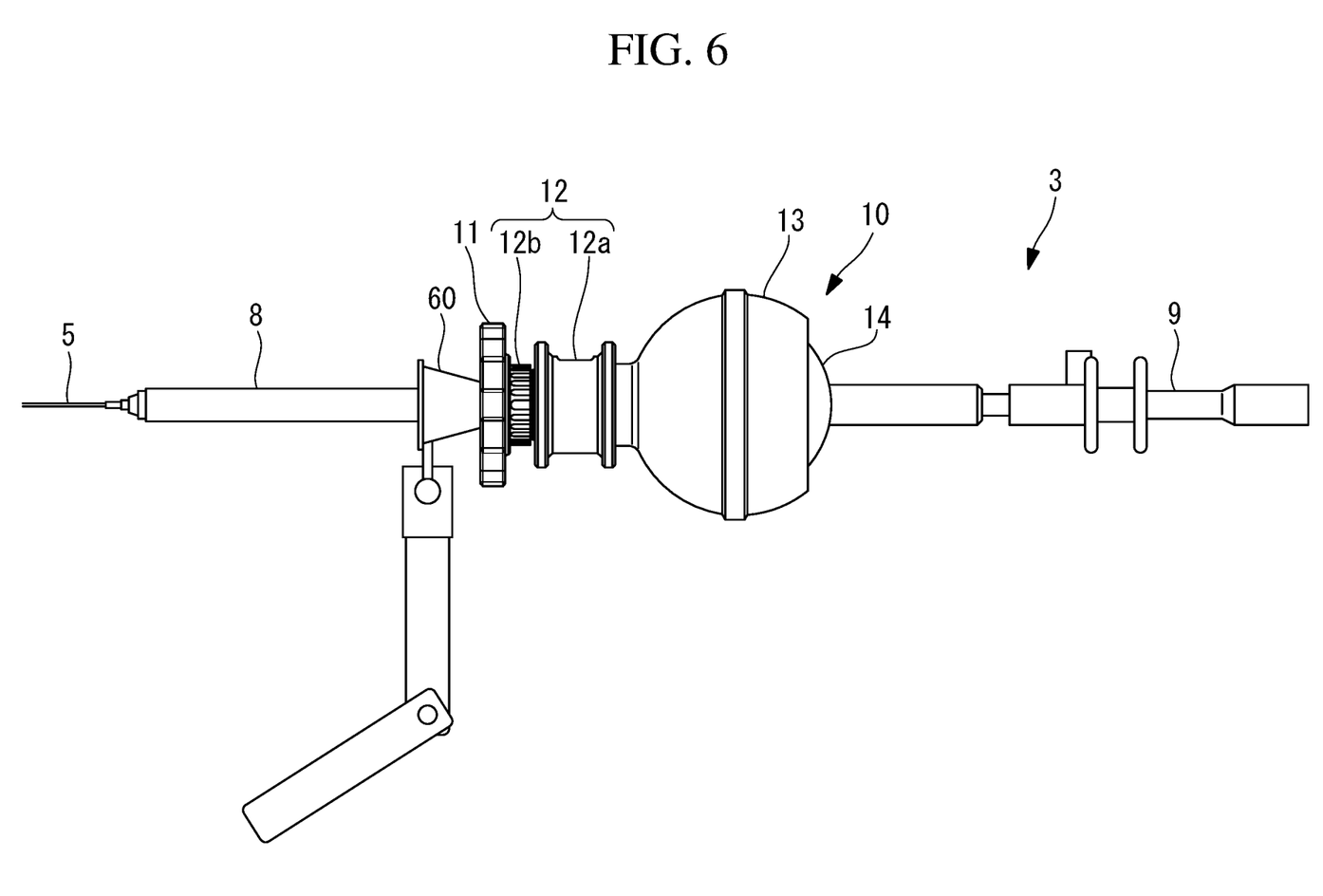
FIG. 6 is a view showing a state in which the treatment tool is held in a treatment-tool holder.

In order to treat the living tissue in the body of the patient Y by using the treatment tool 1 of this embodiment, as shown in FIG. 6, the shaft 2 is inserted into the treatment-tool holder 60, thereby holding the treatment tool 1 at a fixed position with respect to the bed 40. Then, the shaft 2 is inserted into the body via the channel of the endoscope 20 or the external channel attached to the endoscope 20, and the shaft 2 is disposed at a position where the bending section 7 can be observed in an endoscopic image.

In the treatment-tool holder 60, the shaft 2 can be moved in the direction along the longitudinal axis A and can be rotated about the longitudinal axis A. The operator X can advance, retract, and rotate the end effector in the body by moving and rotating the entire treatment tool 1. Furthermore, the operator X can bend the bending section 7 in an arbitrary direction intersecting the longitudinal axis A through a tilt operation of the operation handle 9, and can rotate the shaft 2 about the longitudinal axis A through rotation of the rotation operation part 11, while maintaining the positions of the bending operation part 10 and the operation handle 9 with respect to the treatment-tool holder 60.

Here, when the flexible section 5 is twisted about the longitudinal axis A in the body, this may cause a deviation between a tilt direction of the operation handle 9 (i.e., the direction of rotation of the ball 14) and a bending direction of the bending section 7 in an endoscopic image. Prior to treatment of the living tissue using the end effector, the operator X adjusts the orientation of the bending section 7 about the longitudinal axis A such that the bending section 7 in the endoscopic image is bent in the direction corresponding to the tilt direction of the operation handle 9.

Specifically, the operator X operates the operation handle 9 while viewing the endoscopic image on the display unit 80 and checks whether the bending section 7 is bent in the direction corresponding to the tilt direction of the operation handle 9.

If the bending section 7 is bent in the direction corresponding to the tilt direction of the operation handle 9, the operator X locks the rotation of the rotation operation part 11 by disposing the stopper 12a of the rotation lock part 12 at the lock position, and then performs treatment using the end effector.

On the other hand, if the bending direction of the bending section 7 deviates with respect to the tilt direction of the operation handle 9, the operator X disposes the stopper 12a of the rotation lock part 12 at the release position and rotates the rotation operation part 11 to rotate the shaft 2 about the longitudinal axis A, thereby adjusting the orientation of the bending section 7 about the longitudinal axis A such that the bending section 7 is bent in the direction corresponding to the tilt direction of the operation handle 9. Next, the operator X locks the rotation of the rotation operation part 11 by sliding the stopper 12a up to the lock position, and then performs treatment using the end effector.

When the orientation of the end effector or the bending section 7 about the longitudinal axis A is changed after the rotation operation part 11 is locked by means of the rotation lock part 12, the operator X rotates the entire treatment tool 1 about the longitudinal axis A while maintaining the state in which the rotation of the rotation operation part 11 is locked by means of the stopper 12a. Accordingly, it is possible to change the orientations of the end effector and the bending section 7 while maintaining the adjusted correspondence relationship between the tilt direction of the operation handle 9 and the bending direction of the bending section 7.

In this way, according to this embodiment, the shaft 2 and the bending operation part 10 can be relatively rotated about the longitudinal axis A, and, through rotation of the rotation operation part 11, which is provided between the shaft 2 and the bending operation part 10, the shaft 2 can be rotated about the longitudinal axis A while the orientation of the bending operation part 10 is maintained. Therefore, there is an advantage in that, when a deviation occurs between the tilt direction of the operation handle 9 and the bending direction of the bending section 7, the shaft 2 is rotated through operation of the rotation operation part 11, thereby making it possible to correct the deviation of the bending direction of the bending section 7 with respect to the tilt direction of the operation handle 9. Furthermore, after the bending direction of the bending section 7 is adjusted with respect to the tilt direction of the operation handle 9, the rotation of the rotation operation part 11 is locked by means of the rotation lock part 12, thereby making it possible to operate the entire treatment tool 1 while maintaining the correspondence relationship between the tilt direction of the operation handle 9 and the bending direction of the bending section 7.

In correcting the deviation between the tilt direction of the operation handle 9 and the bending direction of the bending section 7, it is also possible to rotate, instead of the rotation operation part 11, the bending operation part 10 and the operation handle 9 with respect to the rotation operation part 11 and the shafts 2 and 8.

In a case in which the rotation transmission efficiency of the flexible section 5 is low, it is difficult to rotate the bending section 7 through rotation of the rotation operation part 11. In this case, the bending operation part 10 and the operation handle 9 are rotated while the position of the rotation operation part 11 is held, thereby making it possible to efficiently correct the deviation between the tilt direction of the operation handle 9 and the bending direction of the bending section 7.

In this embodiment, it is also possible to further provide a limiter that limits a rotation amount of the rotation operation part 11 with respect to the bending operation part 10 and the operation handle 9.

Figure 7:
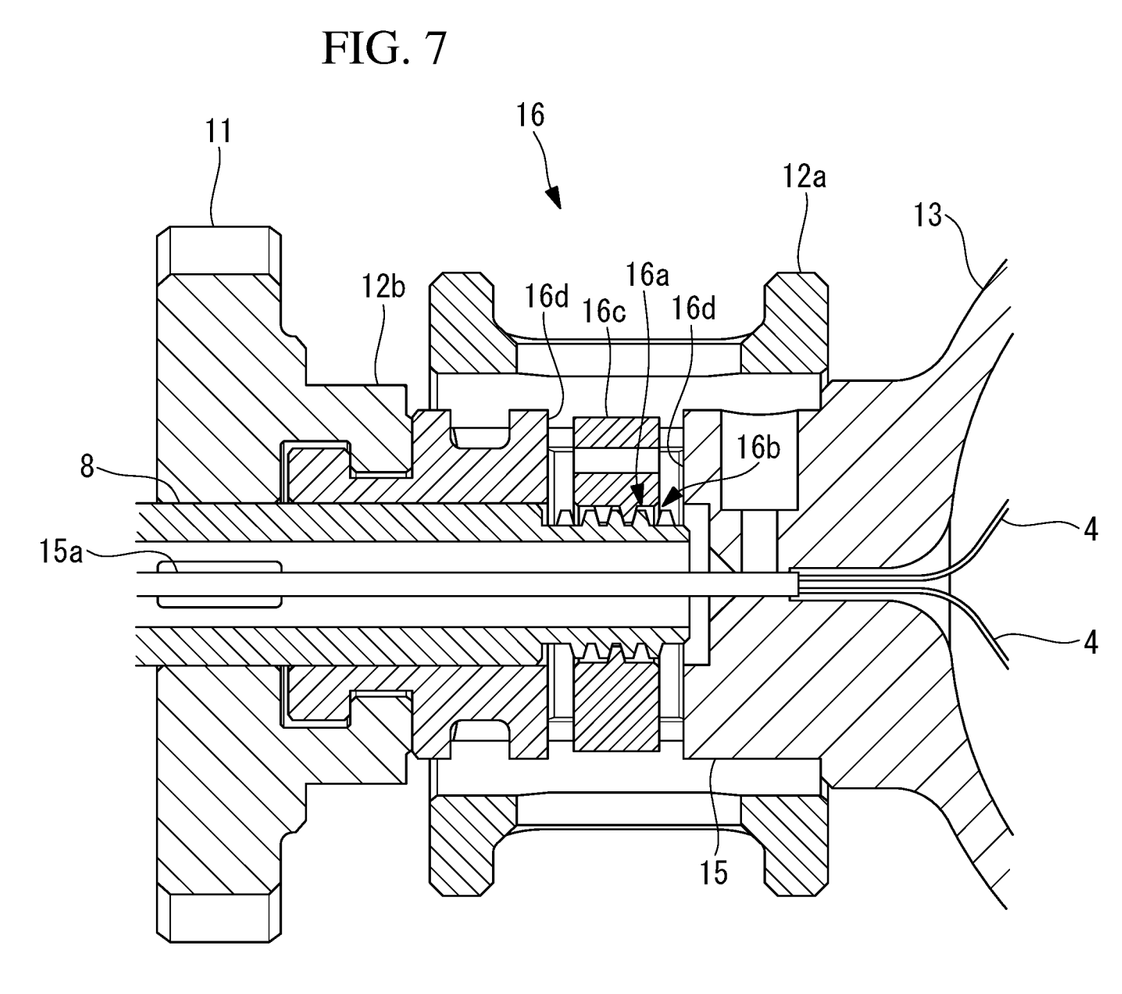
FIG. 7 is a partial longitudinal sectional view of the operation unit, showing the configuration of a limiter.

FIG. 7 shows an example limiter 16. As shown in FIG. 7, the limiter 16 includes: a male screw 16a that is formed at the proximal-end section of the rotating shaft 8 and that is coaxial with the shafts 2 and 8; a round-shaped movable plate (movable body) 16c that has a female screw 16b to be fastened to the male screw 16a and that is linearly moved along the longitudinal axis A through rotation of the shaft 8; and a pair of stopper surfaces (stoppers) 16d that regulate the range of movement of the movable plate 16c.

The pair of stopper surfaces 16d are provided, with a space therebetween in the direction along the longitudinal axis A, at both sides with respect to the movable plate 16c. The movable plate 16c abuts against any one of the stopper surfaces 16d, thereby limiting further movement of the movable plate 16c and also limiting further rotation of the rotation operation part 11.

For example, in a case in which the rotation transmission efficiency of the flexible section 5 is 50%, when the rotation operation part 11 is rotated by 180°, the bending section 7 is rotated by only 90°. In order to be able to adjust the bending section 7 to an arbitrary orientation, the bending section 7 needs to be able to be rotated by 360° or more, regardless of the low rotation transmission efficiency of the flexible section 5. According to the screw-type limiter 16, which is shown in FIG. 7, the rotation angle range of the rotation operation part 11 is determined by the pitches of the screws 16a and 16b and the distance between the pair of stopper surfaces 16d in the direction along the longitudinal axis A. Therefore, it is possible to easily design the maximum rotation amount of the rotation operation part 11 so as to realize the maximum rotation amount of the rotation operation part 11 required in accordance with the rotation transmission efficiency of the flexible section 5. For example, according to the limiter 16, the rotation amount of the rotation operation part 11 can be limited to the range from −360° to +360° inclusive.

Figure 8:
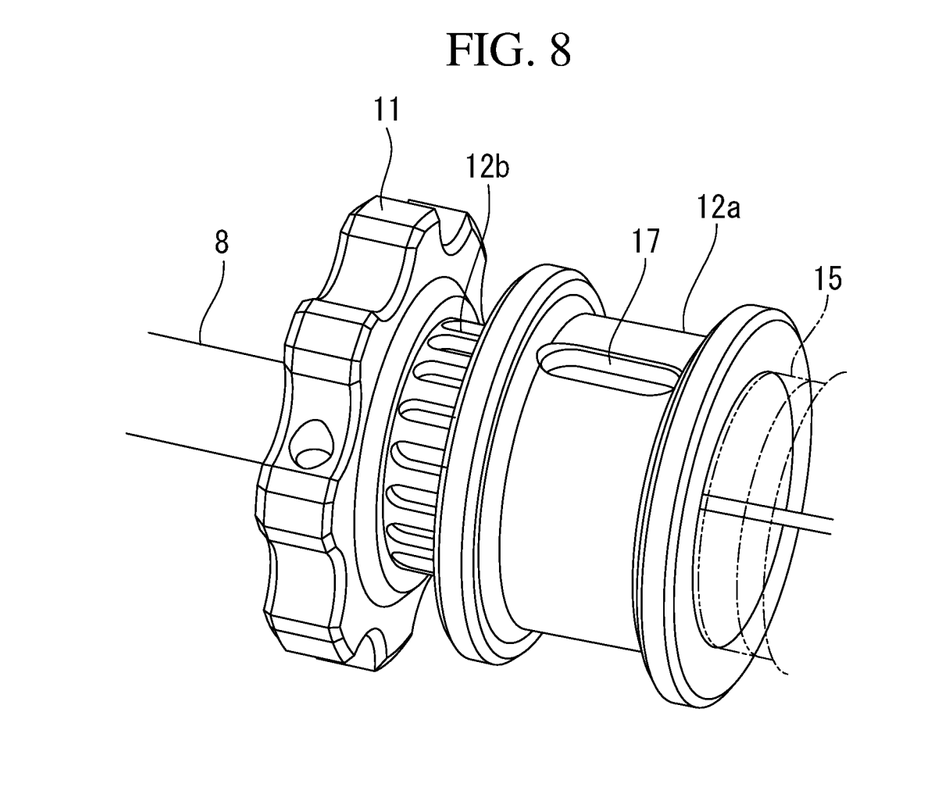
FIG. 8 is a partial perspective view of the operation unit, showing an example indicator.

An indicator for indicating, to the operator X, the position of the movable plate 16c may also be provided in the operation unit 3. As shown in FIG. 8, for example, the indicator may be a window 17 that is provided in the stopper 12a and that allows the movable plate 16c, which is provided inside the stopper 12a, to be seen from outside the stopper 12a. By visibly checking the position of the movable plate 16c between the stopper surfaces 16d, through the window 17, the operator X can grasp the current rotation amount of the rotation operation part 11. Furthermore, because the operator X can determine, from the position of the movable plate 16c, whether the rotation amount of the rotation operation part 11 has reached the maximum rotation amount, it is possible to prevent an excessive force from being applied to the rotation operation part 11 when the rotation operation part 11 is further rotated regardless of the fact that the rotation amount of the rotation operation part 11 has reached the maximum rotation amount.

In this embodiment, it is also possible to further provide a lock holding mechanism that restricts free sliding of the stopper 12a of the rotation lock part 12.

The lock holding mechanism is configured such that, while the stopper 12a is allowed to slide when manually operated by the operator X, the position of the stopper 12a is held in a state in which the operator X is not operating the stopper 12a. By providing this lock holding mechanism, locking of the rotation operation part 11 performed by means of the rotation lock part 12 can be prevented from being unintentionally released.

Figure 9:
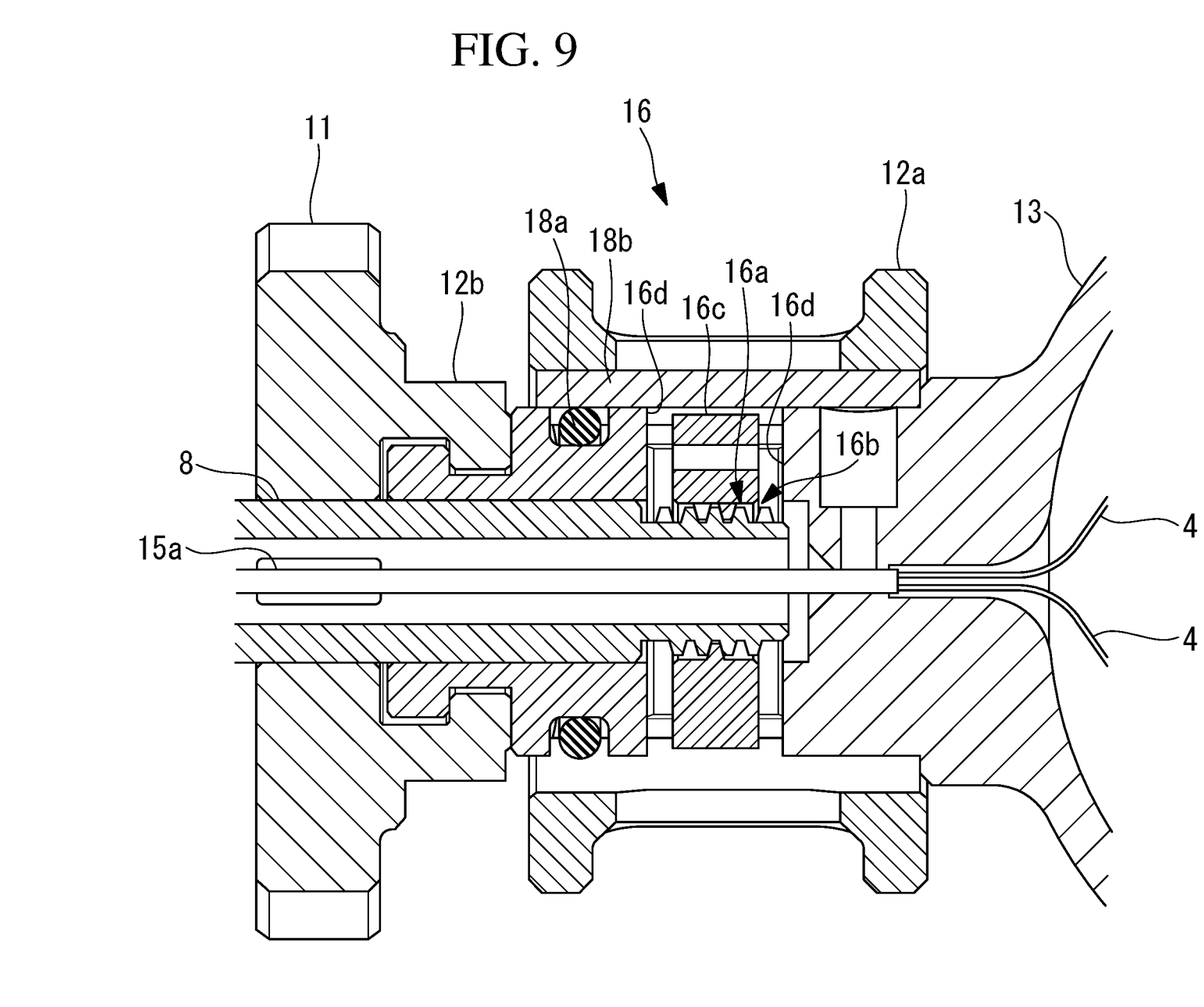
FIG. 9 is a partial longitudinal sectional view of the operation unit, showing an example lock holding mechanism.

As shown in FIG. 9, for example, the lock holding mechanism may be mounted on the outer circumferential surface of the connection sleeve 15 and may be formed of a resin material that produces friction with respect to the inner circumferential surface of the stopper 12a. FIG. 9 shows an example combination of an O-ring 18a and a resin member 18b that is filled in a space between the O-ring 18a and the inner circumferential surface of the stopper 12a. Alternatively, the lock holding mechanism may include a spring that biases the stopper 12a toward the lock position or may include a structure that is closely fitted together with a section of the stopper 12a at each of the lock position and the release position, thus holding the position of the stopper 12a by friction.

In this embodiment, although the ball 14 is rotated through the tilt operation of the operation handle 9, instead of this, it is also possible to rotate the ball 14 through another operation.

Figure 10:
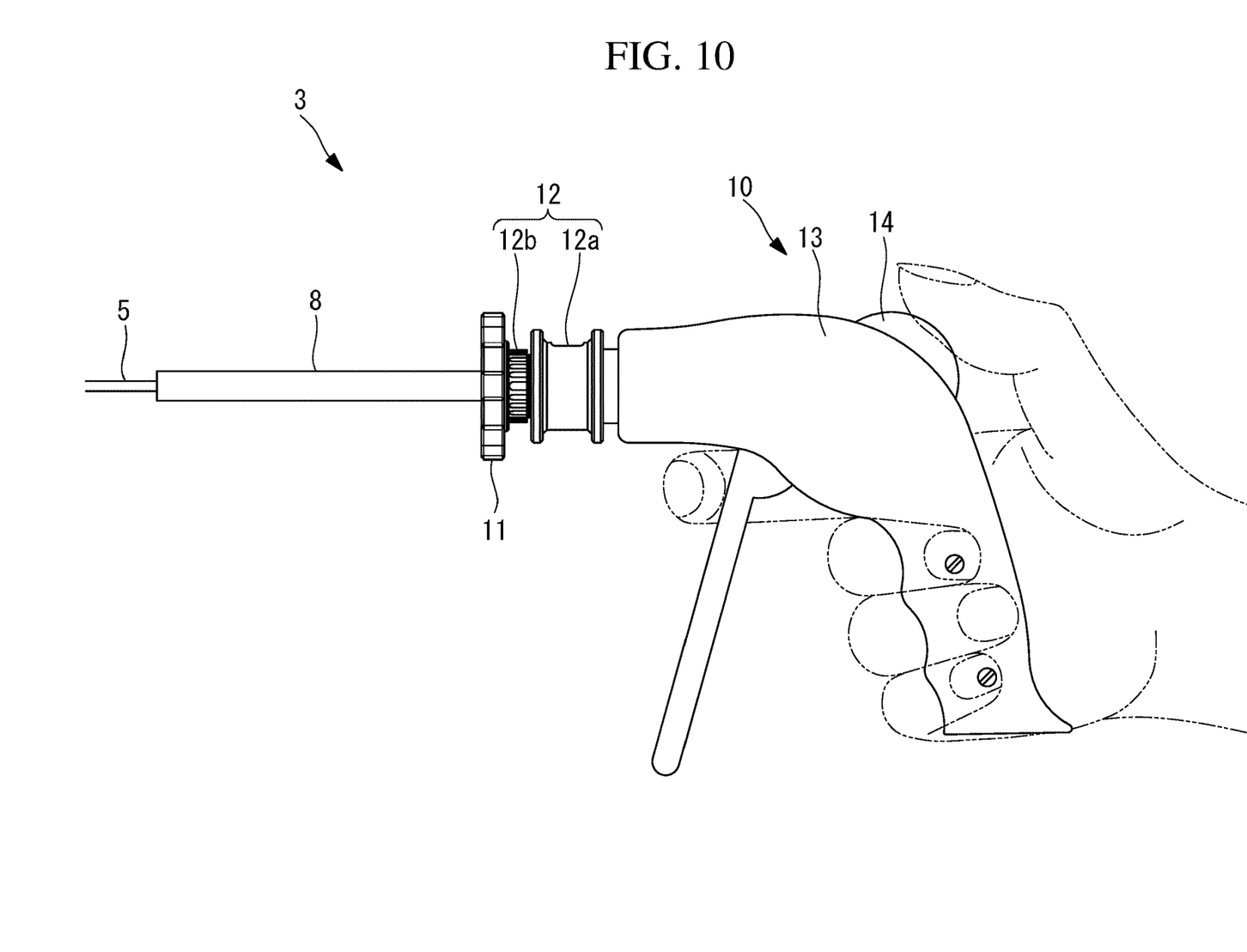
FIG. 10 is a view showing a modification of a bending operation part of the treatment tool shown in FIG. 2.

For example, as shown in FIG. 10, it is also possible to adopt a trackball-type bending operation part 10 in which the ball 14 is directly operated by using a thumb of the operator X.

The invention of a surgical method according to the following features is derived from the above-described embodiment.

Additional Item 1

A surgical method using a treatment tool that includes: an elongated shaft that has a bending mechanism at a distal end thereof; an operation part that is connected to a proximal end of the shaft and that has an operation member capable of pivoting with respect to the shaft; a wire that passes through the inside of the shaft to connect the bending mechanism and the operation member and that is advanced and retracted in a direction along a longitudinal axis of the shaft through pivoting of the operation member, thus bending the bending mechanism; and a rotation mechanism that holds the operation part and the shaft so as to allow relative rotation thereof about the longitudinal axis of the shaft, the surgical method including:

an insertion step of inserting the shaft into a body;

an orientation adjustment step of adjusting, after the insertion step, a relative orientation of the operation member and the bending mechanism about the longitudinal axis by relatively rotating the operation part and the shaft about the longitudinal axis, such that a pivot direction of the operation member and a bending direction of the bending mechanism correspond to each other; and a treatment step of treating living tissue after the adjustment step.

Additional Item 2

A surgical method according to Additional Item 1, further including a rotation lock step of locking, after the adjustment step, relative rotation of the operation part and the shaft about the longitudinal axis.

Additional Item 3

A surgical method according to Additional Item 2, further including a secondary adjustment step of adjusting, after the rotation lock step, the orientations of the bending mechanism and an end effector that is provided at the distal end of the shaft, about the longitudinal axis, in the body, by rotating the entire treatment tool about the longitudinal axis.

The above-described embodiment also leads to the following aspects.

In one aspect, a treatment tool includes: an elongated shaft that has a bending mechanism at a distal end thereof; an operation part that is connected to a proximal end of the shaft and that has an operation member capable of pivoting with respect to the shaft; a wire that passes through the inside of the shaft to connect the bending mechanism and the operation member and that is advanced and retracted in the direction along the longitudinal axis of the shaft through pivoting of the operation member, thus bending the bending mechanism; and a rotation mechanism that holds the operation part and the shaft so as to allow relative rotation thereof about the longitudinal axis of the shaft.

According to this aspect, when the operation member of the operation part is made to pivot, the wire, which extends in the pivot direction of the operation member, is pulled and retracted or is pushed and advanced, thus bending the bending mechanism. Therefore, the bending mechanism can be bent in the direction corresponding to the pivot direction of the operation member.

In this case, because the operation part and the shaft can be relatively rotated about the longitudinal axis by means of the rotation mechanism, it is possible to change the relative orientation of the operation part and the bending mechanism about the longitudinal axis through the relative rotation of the operation part and the shaft. Therefore, a deviation between the pivot direction of the operation member and the bending direction of the bending mechanism can be corrected through the relative rotation of the operation part and the shaft about the longitudinal axis.

In the above-described aspect, in the bending mechanism, the wire may be fixed at a position away from the longitudinal axis in a direction intersecting the longitudinal axis, the bending mechanism may be able to be bent such that the retracted wire is located radially inward, and the shaft may be able to be subjected to twist deformation about the longitudinal axis.

According to this shaft, a deviation between the pivot direction of the operation member and the bending direction of the bending mechanism tends to occur due to twisting of the shaft about the longitudinal axis. Therefore, the rotation mechanism is particularly suitable for a treatment tool that includes such a shaft.

The above-described aspect may further include a lock mechanism that locks relative rotation of the shaft and the operation part relative to each other about the longitudinal axis.

After the correspondence relationship between the pivot direction of the operation member and the bending direction of the bending mechanism is adjusted, the relative rotation of the shaft and the operation part is locked by means of the lock mechanism, thereby making it possible to easily rotate the entire treatment tool while maintaining the correspondence relationship between the pivot direction of the operation member and the bending direction of the bending mechanism.

In the above-described aspect, the shaft may include an inner sheath into which the wire is inserted; a proximal-end section of the inner sheath may be fixed with respect to the operation part at a position between the shaft and the operation member; and the wire may be drawn from the proximal-end section of the inner sheath and may be connected to the operation member.

When the shaft and the operation part are relatively rotated, because the proximal-end section of the inner sheath is fixed with respect to the operation part, the wire is not twisted about the longitudinal axis, between the proximal-end section of the inner sheath and the operation member. Accordingly, a change in the path length of the wire caused by the relative rotation of the shaft and the operation part can be suppressed. Furthermore, in a case in which a plurality of wires are provided, it is possible to prevent entanglement of the wires between the shaft and the operation member.

The above-described aspect may further include a limiter that limits the amount of relative rotation of the operation part and the shaft about the longitudinal axis.

By doing so, it is possible to prevent excessive twisting of the wire caused by excessive relative rotation of the operation part and the shaft.

In the above-described aspect, the limiter may include: a male screw that is provided so as to be coaxial with the shaft and that is rotated integrally with the shaft; a movable body that has a female screw to be fastened to the male screw and that is linearly moved along the longitudinal axis through rotation of the shaft; and a pair of stoppers that are disposed, with a space therebetween in the direction along the longitudinal axis, at both sides with respect to the movable body.

When the male screw is rotated with respect to the operation part through rotation of the shaft, the movable body, which is fastened to the male screw in the female screw thereof, is linearly moved along the longitudinal axis. The rotation of the shaft is limited at a position where the movable body abuts against one of the stoppers. Specifically, the maximum rotation amount of the shaft is determined by the pitches of the male screw and the female screw and the distance between the pair of stoppers in the direction along the longitudinal axis. Therefore, a desired maximum relative-rotation amount of the shaft and the operation part can be easily realized.

REFERENCE SIGNS LIST 1 treatment tool
2 shaft
3 operation unit
4 wire
5 flexible section
5a inner sheath
5b outer sheath
6 distal-end section
7 bending section (bending mechanism)
8 rotating shaft
9 operation handle (operation member)
10 bending operation part
11 rotation operation part
12 rotation lock part (lock mechanism)
12a stopper
12b engagement ring
12c protrusion
12d engagement protrusion
12e groove
13 socket
14 ball (operation member)
15 connection sleeve (rotation mechanism)
15a guide protrusion
16 limiter
16a male screw
16b female screw
16c movable plate (movable body)
16d stopper surface (stopper)
17 window (indicator)
18a O-ring (lock holding mechanism)
18b resin member (lock holding mechanism)
19 fixing part
20 endoscope
40 bed
60 treatment-tool holder
80 display unit

The invention claimed is:

1. A treatment tool comprising:
an elongated shaft that has a bending section at a distal end thereof;
a bending operation part comprising a ball-joint structure and that is connected to a proximal-end side of the elongated shaft and configured to operate the bending section;
a rotatable shaft that is provided at a distal-end of the bending operating part so as to be coaxial with the elongated shaft;
a connection sleeve that is provided at a connection section of the bending operation part where the bending operation part and the rotatable shaft are connected, and that rotatably holds the rotatable shaft;
a rotating handle that is provided at the proximal-end side of the elongated shaft and that is configured to rotate the rotatable shaft;
a stopper that is slidable along an outside of the connection sleeve in a direction of a longitudinal axis of the elongated shaft and that is configured to engage with both the rotating handle and the connection sleeve at a lock position in a range of movement of the rotating handle, thereby locking rotation of the rotatable shaft with respect to the connection sleeve;
a wire that connects the bending section and the bending operation part and that is advanced and retracted in a direction along the longitudinal axis of the rotatable shaft in accordance with an operation of the bending operation part, thus bending the bending section;
an inner sheath through which the wire extends, inside the rotatable shaft; and
an outer sheath having a proximal-end section that is connected to a distal-end section of the rotatable shaft so that the outer sheath is rotatable together with the rotatable shaft;
wherein:
a distal-end section of the inner sheath is fixed to a distal-end section of the outer sheath; and
a proximal-end section of the inner sheath is rotatable with respect to the outer sheath.

2. A treatment tool according to claim 1, further comprising:
a guide protrusion that is provided on the connection sleeve, that allows sliding movement of the stopper regardless of a position of the stopper, and that is engaged with the stopper so as to prevent rotational movement of the stopper; and
an engagement ring that is provided on the rotating handle and that is configured to engage with the stopper so as to prevent rotational movement of the rotating handle when the stopper is positioned at the lock position.

3. A treatment tool according to claim 2, further comprising:
a pair of engagement protrusions provided on an inner circumferential surface of the stopper and spaced apart in a circumferential direction of the stopper,
wherein the guide protrusion is fitted between the pair of engagement protrusions so as to prevent rotational movement of the stopper.

4. A treatment tool according to claim 2, wherein the engagement ring comprises a plurality of grooves at fixed intervals in a circumferential direction of the rotating handle.

5. A treatment tool according to claim 4, further comprising:
locking protrusions provided on an inner circumferential surface of the stopper in a circumferential direction of the stopper,
wherein the locking protrusions are fitted into the grooves so as to prevent rotational movement of the rotating handle when the stopper is positioned at the lock position.

6. A treatment tool according to claim 1, further comprising:
a limiter that is provided at a connection section of the elongated shaft and the connection sleeve, the limiter comprising a movable plate that restricts a rotation amount of the rotating handle.

7. A treatment tool according to claim 6, wherein the limiter further comprises:
a male screw that is provided at a proximal-end section of the elongated shaft so as to be coaxial with the elongated shaft and that is configured to be rotated integrally with the elongated shaft; and
a pair of surfaces that are disposed, with a space between the surfaces, at both sides of the movable plate in the direction along the longitudinal axis, wherein the movable plate comprises a female screw that is screwed together with the male screw so that the movable plate is movable along the longitudinal axis through the rotation of the elongated shaft.

8. A treatment tool according to claim 1, wherein the stopper comprises a window that allows a rotation amount of the elongated shaft with respect to the connection sleeve to be visually recognized.

9. A treatment tool according to claim 6, wherein the stopper comprises a window through which a position of the movable plate can be visually observed.

10. A treatment tool according to claim 1, wherein the stopper is configured to be held in place with respect to the connection sleeve in a state in which an operator is not operating the stopper.

11. A treatment tool according to claim 10, wherein the stopper is configured to be held in place by friction between the stopper and the connection sleeve in the state in which the operator is not operating the stopper.

12. A treatment tool according to claim 10, wherein the stopper is biased toward the lock position when in the state in which the operator is not operating the stopper.

13. A treatment tool according to claim 1,
wherein:
a proximal-end section of the inner sheath is fixed with respect to the bending operation part at a position further toward the proximal end than the rotatable shaft; and
the wire extends from the proximal-end section of the inner sheath to connect to the bending operation part.

14. A treatment tool according to claim 1, wherein:
the inner sheath is a multi-lumen sheath disposed within the rotatable shaft; and
a plurality of wires that extend through lumens of the multi-lumen sheath on a one-to-one basis and that respectively correspond to different sides of the bending section, wherein each of the wires connects the bending section and the bending operation part and is advanced and retracted in a direction along the longitudinal axis of the rotatable shaft in accordance with an operation of the bending operation part, thus bending the bending section in a direction corresponding to the respective side of the bending section.

15. An operation method for a treatment tool, the treatment tool including:
an elongated shaft that has a bending section at a distal end thereof;
a rotatable shaft that is provided at a distal-end of the bending operation part so as to be coaxial with the elongated shaft;
a bending operation part comprising a ball-joint structure and that rotatably holds the rotatable shaft at a proximal-end side of the rotatable shaft and is configured to perform a bending operation on the bending section;
a rotating handle that is provided on the elongated shaft and that is configured to rotate the rotatable shaft;
a wire that connects the bending section and the bending operation part and that is advanced and retracted in a direction along the longitudinal axis of the rotatable shaft in accordance with an operation of the bending operation part, thus bending the bending section;
an inner sheath through which the wire extends, inside the rotatable shaft; and
an outer sheath having a proximal-end section that is connected to a distal-end section of the rotatable shaft so that the outer sheath is rotatable together with the rotatable shaft;
wherein:
a distal-end section of the inner sheath is fixed to a distal-end section of the outer sheath; and
a proximal-end section of the inner sheath is rotatable with respect to the outer sheath,
the operation method comprising:
locking rotation of the rotatable shaft by the rotating handle with respect to the bending operation part;
inserting the elongated shaft into a body of a patient;
after inserting the elongated shaft into the body of the patient, releasing the lock when a deviation occurs in a correspondence relationship between operation of the bending operation part and a bending direction of the bending section due to twisting of the rotatable shaft;
in a state in which the lock has been released, rotating the rotatable shaft, through operation of the rotating handle, with respect to the bending operation part, thereby adjusting the correspondence relationship between the operation of the bending operation part and the bending direction of the bending section; and
locking again the rotation of the rotatable shaft by the rotating handle.

16. A treatment tool according to claim 1, further comprising:
a lock holding mechanism mounted onto an outer circumferential surface of the connection sleeve and configured to produce friction with respect to the stopper, the lock holding member comprising:
a ring member disposed on the outer circumferential surface of the connection sleeve; and
a resin member disposed between the ring member and an inner circumferential surface of the stopper.

* * * * *